United States Patent [19]

Varma et al.

[11] 4,146,538
[45] Mar. 27, 1979

[54] 17-ALKYLTHIO (AND ARYLTHIO) ANDROSTENO[17α,16α-B]BENZOPYRAN-3-ONES AND [16α,17α-B]NAPHTHOPYRAN-3-ONES

[75] Inventors: Ravi K. Varma, Belle Mead; Sam T. Chao, East Windsor, both of N.J.

[73] Assignee: E. R. Squibb & Sons, Inc., Princeton, N.J.

[21] Appl. No.: 881,486

[22] Filed: Feb. 27, 1978

[51] Int. Cl.² .............................................. C07J 1/00
[52] U.S. Cl. ........................ 260/239.55 R; 260/397.3; 260/397.45; 424/278
[58] Field of Search ......................................................
/Machine Searched Steroids

[56] References Cited
U.S. PATENT DOCUMENTS

| 3,971,772 | 7/1976 | Cimarusti et al. | 260/239.55 R |
| 4,002,614 | 1/1977 | Anner et al. | 260/239.55 R X |

Primary Examiner—Ethel G. Love
Attorney, Agent, or Firm—Lawrence S. Levinson; Merle J. Smith; Donald J. Barrack

[57] ABSTRACT

Steroids having the formula

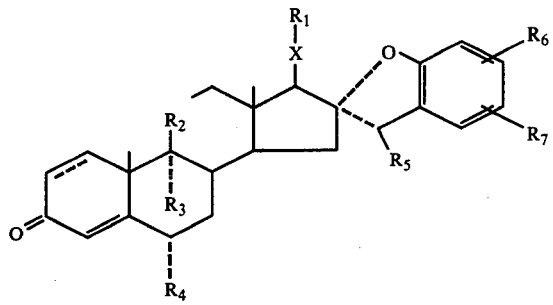

wherein X is -S-,

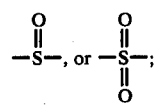

$R_1$ is alkyl, aryl or acyloxyalkyl; $R_2$ is carbonyl or β-hydroxymethylene; $R_3$ is hydrogen or halogen; $R_4$ is hydrogen, fluorine or methyl; $R_5$ is hydrogen or alkyl; and $R_6$ and $R_7$ are the same or different and are hydrogen, halogen, alkyl or alkoxy, or $R_6$ and $R_7$ together with the benzene ring to which they are attached form a naphthalene group; can be used as antiinflammatory agents.

17 Claims, No Drawings

17-ALKYLTHIO (AND ARYLTHIO) ANDROSTENO[17α,16α-B]BENZOPYRAN-3-ONES AND [16α,17α-B]NAPHTHOPYRAN-3-ONES

BACKGROUND OF THE INVENTION

Steroids having one or more additional rings fused in the 16,17-positions are known in the art of antiinflammatory steroids. Exemplary disclosures of such steroids are U.S. Pat. No. 3,048,581 which discloses 16,17-cyclic acetals and ketals of certain pregnenes; U.S. Pat. Nos. 3,937,720 and 3,994,935 which disclose steroidal[-16α,17-b]-naphthalenes, the steroids being of the pregnene series; U.S. Pat. No. 3,944,584 which discloses steroidal[16α,17-d]-cyclohexenes, the steroids being of the pregnene series; U.S. Pat. No. 3,945,997 which discloses steroidal bicyclic dioxanes, the dioxane ring being fused in the 16,17-position and the steroids being of the pregnene series; U.S. Pat. Nos. 3,971,772 and 3,971,773 which disclose steroidal[16α,17-b][1,4]dioxanes and steroidal[16α,17-b]-[1,4]dioxins, the steroids being of the pregnene series; U.S. Pat. No. 3,979,417 which discloses 1'H-androsta[16,17]cyclopentene-3-ones; U.S. Pat. No. 4,018,757 which discloses steroidal[16α,17-c][2H]pyrroles, the steroids being of the pregnene series; and U.S. Pat. No. 4,018,774 which discloses steroidal[16α,17-d]isoxazolidines, the steroids being of the pregnene series.

RELATED APPLICATIONS

Copending U.S. Pat. application Ser. No. 796,293 filed May 12, 1977, now U.S. Pat. No. 4,094,840, discloses 17-alkylthio (and arylthio)androsteno[16α,17α-b]benzodioxin-3-ones. Copending U.S. patent application Ser. No. 796,292 filed May 12, 1977, now U.S. Pat. No. 4,091,036, discloses 17-alkylthio (and arylthio)-1',2',3',4'-tetrahydroandrosteno[16α,17α-b]naphthalenes.

BRIEF DESCRIPTION OF THE INVENTION

Steroids having the formula

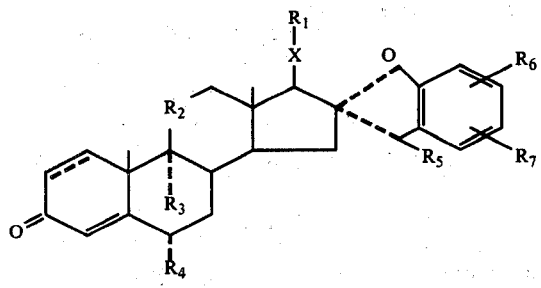

can be utilized as antiinflammatory agents. In formula I, and throughout the specification, the symbols are as defined below.

X is -S-,

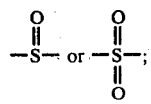

$R_1$ is alkyl, aryl or acyloxyalkyl;
$R_2$ is carbonyl or β-hydroxymethylene;
$R_3$ is hydrogen or halogen;
$R_4$ is hydrogen, fluorine or methyl;
$R_5$ is hydrogen or alkyl; and
$R_6$ and $R_7$ are the same or different and are hydrogen, halogen, alkyl or alkoxy, or $R_6$ and $R_7$ together with the benzene ring to which they are attached form a naphthalene group.

A dotted line in the 1,2-position of a structural formula in this disclosure indicates the optional presence of ethylenic unsaturation.

The term "aryl", as used throughout the specification, refers to phenyl or phenyl substituted with one or two alkyl, alkoxy or halogen groups.

The term "halogen", as used throughout the specification, refers to fluorine, chlorine, bromine and iodine.

The terms "alkyl" and "alkoxy", as used throughout the specification, refer to groups having 1 to 10 carbon atoms.

The term "acyloxyalkyl", as used throughout the specification, refers to a group having the formula

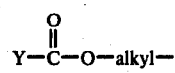

wherein Y is alkyl or aryl.

DETAILED DESCRIPTION OF THE INVENTION

The steroids of this invention can be prepared utilizing as starting materials androstenes having the formula

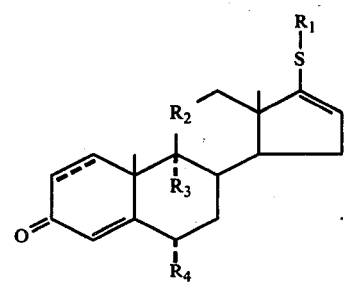

The androstenes of formula II are prepared according to the procedure disclosed in copending U.S. patent applications Ser. No. 796,292, filed May 12, 1977 and Ser. No. 796,293, filed May 12, 1977. An androstene having the formula

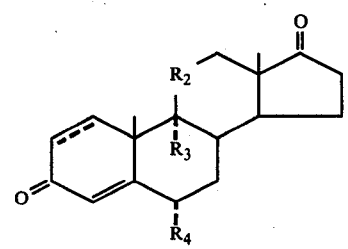

can be reacted with a thiol compound having the formula

in the presence of a Lewis acid (e.g., boron trifluoride etherate) to yield a steroid having the formula

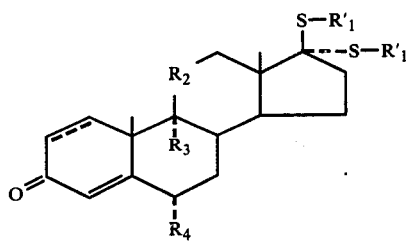

V

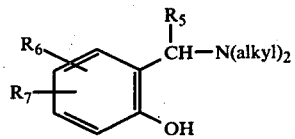

VIII yields the corresponding steroid product having the formula

In formulas IV and V, and throughout the specification, the symbol $R'_1$ is alkyl or aryl. The reaction can be run in an organic solvent (e.g., a halogenated hydrocarbon) or mixture of organic solvents. The use of some glacial acetic acid improves yields. Reaction conditions are not critical, and the reaction can be conveniently run at room temperature, preferably in an inert atmosphere (e.g., argon or nitrogen). Better yields may be obtained with relatively short reaction times (less than 1 hour).

An androstene of formula V can be converted to the corresponding steroid of formula II by simply heating the steroid in an inert solvent (e.g., diethylbenzene or dichlorobenzene). A temperature of about 180° C. is preferred.

Those steroids of formula II wherein $R_1$ is acyloxyalkyl are prepared by first oxidizing a corresponding steroid of formula II, wherein $R_1$ is alkyl, using one equivalent of oxidizing agent, to obtain a steroid having the formula

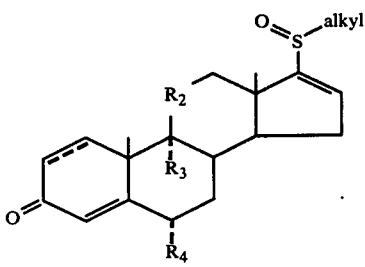

VI

A 17-alkylsulfinyl steroid of formula VI can be reacted with an appropriate acid anhydride, and a basic catalyst such as the sodium salt of the corresponding acid, to yield the corresponding 17-[[(acyloxy)alkyl]thio]steroid of formula II, i.e., a steroid having the formula

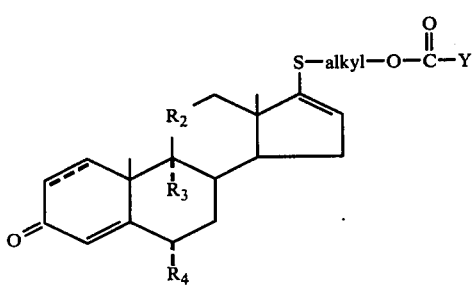

VII

Reaction of an androstene of formula II with a compound having the formula

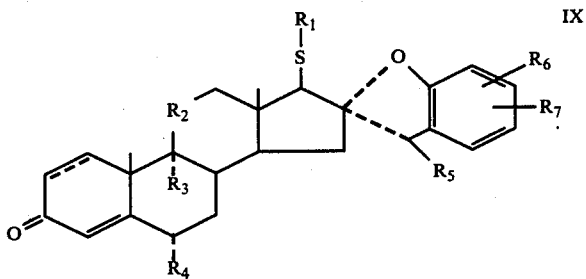

IX

The reaction can be run in an organic solvent, e.g., an aromatic solvent such as mesitylene, at the reflux temperature of the solvent.

Oxidation of an androstene of formula IX with a peracid (e.g., m-chloroperbenzoic acid), a peracid salt (e.g., sodium-m-periodate), a peroxide (e.g., hydrogen peroxide) or air yields the corresponding sulfinyl steroid or the corresponding sulfonyl steroid; i.e., the corresponding products of formula I wherein X is

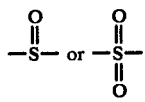

respectively. The use of one equivalent of oxidizing agent will yield predominantly a sulfinyl steroid and the use of two or more equivalents of oxidizing agent will yield predominantly a sulfonyl steroid. Metachloroperbenzoic acid is the preferred oxidizing agent. The oxidation reaction can be run in an organic solvent, e.g., a halogenated hydrocarbon such as chloroform. Alternatively, the sulfonyl steroids of formula I can be prepared by oxidizing the corresponding sulfinyl steroids of formula I.

The oxidation of a 17-thio product to yield a 17-sulfinyl steroid of formula I results in a mixture of two isomers which can be separated using conventional techniques.

The steroids of formula I can be used in lieu of known glucocorticoids in the treatment of inflammatory conditions; e.g., rheumatoid arthritis. They can be administered in the same manner as hydrocortisone, the dosage being adjusted for the relative potency of the particular steroid. Additionally, the steroids of this invention can be used topically in lieu of known glucocorticoids in the treatment of skin conditions such as dermatitis, psoriasis, sunburn, neurodermatitis, eczema or anogenital pruritus.

When given orally, the steroids of this invention may be used in a dosage range of 0.1 to 200 milligrams, preferably 0.3 to 100 milligrams, for a 70 kg. mammal. If administered topically, the steroids of this invention may be used in the range of 0.01 to 5.0% by weight, preferably 0.025 to 2.0% by weight, in a conventional cream, ointment, lotion or the like.

The following examples are specific embodiments of this invention.

EXAMPLE 1

17-[[(Acetyloxy)methyl]thio]-9-fluoro-3',4'-dihydro-11β-hydroxy-2'H-androsta-1,4-dieno[17α,16α-b][1]-benzopyran-3-one

(A)
9-Fluoro-11β-hydroxy-17,17-bis(methylthio)androsta-1,4-diene-3-one

A solution of 9-fluoro-11β-hydroxyandrosta-1,4-diene-3,17-dione (2.0 g) in glacial acetic acid (25 ml) is mixed at room temperature with a solution of methanethiol (2.4 g) in dichloromethane (16 ml) and boron trifluoride etherate (0.5 ml). After 1.5 hours, the mixture is poured into water and diluted with chloroform. The organic layer is then separated, washed with a dilute sodium bicarbonate solution and water, dried and evaporated in vacuo. The residue is absorbed on a column of silica gel (50 g). Elution of the column with chloroform removes the non-steroidal impurities and a product resulting from thiol addition to $\Delta^1$. Subsequent elution with chloroform affords the desired material as a solid (957 mg). Finally, elution with chloroform-ethyl acetate (95:5) affords the unreacted steroid (345 mg). A specimen of the 957 mg solid is crystallized once from chloroform-methanol to afford the analytical sample of the title compound, melting point 305° C. (dec.).

(B)
9-Fluoro-11β-hydroxy-17-(methylthio)androsta-1,4,16-trien-3-one

A suspension of 9-fluoro-11β-hydroxy-17,17-bis(methylthio)androsta-1,4-diene-3-one (3.6 g) in diethylbenzene (250 ml) is slowly distilled from a bath at 220° C. In a few minutes, a clear solution results and the starting material disappears. On cooling in an ice bath, the solution deposits small needles of the analytical specimen of the title compound, (2.9 g), melting point 268° C. (dec.). (discoloration starts at 263° C.).

(C)
9-Fluoro-11β-hydroxy-17-(methylsulfinyl)androsta-1,4,16-trien-3-one

To a stirred solution of 1.0 g of 9-fluoro-11β-hydroxy-17-(methylthio)androsta-1,4,16-trien-3-one in chloroform (500 ml) is added a solution of 85% m-chloroperbenzoic acid (552 mg) in chloroform (100 ml) in the course of 3.0 minutes. In less than 10 minutes, the peracid and the starting steroid disappear. The solution is then washed with a dilute potassium carbonate solution and water, dried, concentrated (to about 10 ml) and diluted with ethyl acetate resulting in the precipitation of small, light needles of the analytical specimen of the title compound, (1.0 g), melting point 268°-269° C. (dec.). This is a mixture of the two sulfinyl isomers.

(D)
17-[[(Acetyloxy)methyl]thio]-9-fluoro-11β-hydroxyandrosta-1,4,16-trien-3-one A mixture of 1.5 g of 9-fluoro-11β-hydroxy-17-(methylsulfinyl)androsta-1,4,16-trien-3-one, 70 ml of acetic anhydride and 2 g of fused sodium acetate is heated at 110° C. under nitrogen for 2 hours. The acetic anhydride is partially removed by distillation under vacuum and the resulting slurry is diluted with 1:1 chloroform-water. The organic layer is separated, washed with diluted sodium bicarbonate solution, water, dried over anhydrous sodium sulfate and evaporated in vacuo. The residue is dissolved in 4:1 chloroform-hexane and chromatographed on a 40 g-silica gel column. Elution with 1:4 hexane-chloroform gives 940 mg of slightly impure material. Two crystallizations from acetone-hexane give 350 mg of the title compound, melting point 193°-194° C., with consistent spectral data.

(E)
17-[[(Acetyloxy)methyl]thio]-9-fluoro-3',4'-dihydro-11β-hydroxy-2'H-androsta-1,4-dieno[17α,16α-b][1]-benzopyran-3-one A solution of 17-[[(acetyloxy)methyl]thio]-9-fluoro-11β-hydroxyandrosta-1,4,16-triene-3-one (1.1 g) and ortho-dimethylaminomethylphenol (800 mg) in dry mesitylene is refluxed under an atmosphere of nitrogen for 48 hours when the starting steroid disappears almost completely as shown by thin-layer chromatography. The mesitylene is then removed by distillation in vacuo; the residue is dissolved in chloroform, washed with cold 0.5N hydrochloric acid, a dilute sodium bicarbonate solution, and water, dried and evaporated. The residue is subjected to a column chromatography over silica gel (25 g) using chloroform-hexane mixtures, chloroform and chloroform-ethylacetate mixtures for elution to afford, in the chloroform fractions, 900 mg of the title compound contaminated with a small amount of the starting steroid. One crystallization of this from ethyl acetate affords the analytical specimen (520 mg) of the title compound, melting point 253°-254° C. (dec.) (discoloration starts from 250° C.) with consistent spectral data.

EXAMPLE 2

17-(Ethylthio)-9-fluoro-3',4'-dihydro-11β-hydroxy-2'H-androsta-1,4-dieno[17α,16α-b][1]benzopyran-3-one

(A)
17,17-Bis(ethylthio)-9-fluoro-11β-hydroxyandrosta-1,4-diene-3-one

A solution of 9.5 g of 9-fluoro-11β-hydroxyandrosta-1,4-diene-3,17-dione in 50 ml of dichloromethane and 50 ml of glacial acetic acid is stirred with 11.2 g of ethanethiol and 7.5 ml of boron trifluoride etherate at room temperature under nitrogen. After 1.5 hours the solution is diluted with 350 ml of chloroform. The chloroform solution is washed with water, saturated sodium bicarbonate solution and water, dried over anhydrous sodium sulfate and evaporated in vacuo to give 11 g of a foam. This is dissolved in hexane-chloroform (2:1) and chromatographed on a 200 g-silica gel column. Elution with hexane-chloroform (2:1 and 1:1) gives 2.1 g of a tlc-homogeneous material. Crystallization from acetone-hexane gives 1.05 g of the title compound, melting point 276°-277° C., dec.

(B)
17-(Ethylthio)-9-fluoro-11β-hydroxyandrosta-1,4,16-trien-3-one

A suspension of 1.8 g of 17,17-bis(ethylthio)-9-fluoro-11β-hydroxyandrosta-1,4-dien-3-one in 120 ml of diethylbenzene is stirred at 190° C. (oil bath temperature) for 1 hour. The solution is cooled to 0° C. and the solid that precipitates is filtered. This is redissolved in 1:9 hexane-chloroform and chromatographed on a 60 g-silica gel column. Elution with 1:9 hexane-chloroform gives 1.35 g of a tlc-homogeneous material. Crystallization from chloroform-methanol gives 680 mg of the title compound, melting point 282°–283° C., dec.

(C)

17-(Ethylthio)-9-fluoro-3',4'-dihydro-11β-hydroxy-2'H-androsta-1,4-dieno[17α,16α-b][1]benzopyran-3-one A solution of 1.07 g of 17-(ethylthio)-9-fluoro-11β-hydroxyandrosta-1,4,16-triene-3-one in 120 ml of dry mesitylene is stirred at 168°–170° C. under nitrogen for about 16 hours with o-dimethylaminomethylphenol. More o-dimethylaminomethylphenol (900 mg) is added and the solution is stirred at 175°–180° C. under nitrogen. After 20 hours some more o-dimethylaminomethylphenol (400 mg) is added and the solution is stirred at 175°–180° C. under nitrogen for another 6 hours. It is then cooled and 75 ml of mesitylene is distilled off. The oily residue is passed through a short silica gel (60 g) column. Elution with chloroform gives mesitylene, 1.05 g of a gummy material and some o-dimethylaminophenol. The gummy material is redissolved in 9:1 chloroform-hexane and chromatographed on a 100 g-silica gel column. Elution with 1:1 hexane-chloroform gives 910 mg of the desired compound contaminated with some o-dimethylaminophenol. This is redissolved in chloroform, washed with 5% hydrochloric acid solution and water, dried over anhydrous sodium sulfate and evaporated in vacuo to give 800 mg of material. Three crystallizations from acetone-hexane give 340 mg of the analytical specimen of the title compound, melting point 249°–252° C., with consistent spectral data.

EXAMPLE 3

17-(Phenylthio)-9-fluoro-2',3'-dihydro-11β-hydroxy-1'H-androsta-1,4-dieno[16α,17α-b]naphtho[1,2-e]pyran-3-one (A)

9-Fluoro-11β-hydroxy-17,17-bis(phenylthio)-androsta-1,4-dien-3-one

A solution of 9.0 g of 9-fluoro-11β-hydroxy-androsta-1,4-diene-3,17-dione in 50 ml of dichloromethane and 50 ml of glacial acetic acid is stirred with 18.68 g of thiophenol and 7.5 ml of boron trifluoride etherate at room temperature under nitrogen. After 50 minutes the solution is diluted with 350 ml of chloroform. The chloroform solution is washed successively with water, saturated sodium bicarbonate solution and water, dried over anhydrous sodium sulfate and evaporated in vacuo to give 11.6 g of an oil. This is dissolved in 1:3 hexane-chloroform and chromatographed on a 200 g-silica gel column. Elution with 1:3 hexane-chloroform and chloroform gives unreacted starting steroid and 3.5 g of a tlc-homogeneous material. Crystallization of the 3.5 g of material from chloroform-methanol gives 2.0 g of the title compound, melting point 249°–250° C. (dec.).

(B)

9-Fluoro-11β-hydroxy-17-(phenylthio)androsta-1,4,16-trien-3-one

A suspension of 3.0 g of 9-fluoro-11β-hydroxy-17,17-bis(phenylthio)androsta-1,4-dien-3-one in 150 ml of diethylbenzene is stirred at 190° C. for 45 minutes. The solution is cooled at 0° C. and a solid crystallizes. This is filtered and dried in vacuo to give 2.3 g of material. Recrystallization from chloroform-methanol gives 1.1 g of the title compound, melting point 250°–251° C. (dec.).

(C)

17-(Phenylthio)-9-fluoro-2',3'-dihydro-11β-hydroxy-1'H-androsta-1,4-dieno[16α,17α-b]naphtho[1,2-e]pyran-3-one A solution of 9-fluoro-11β-hydroxy-17-(phenylthio)-androsta-1,4,16-triene-3-one (100 mg) in dry mesitylene (15 ml) is refluxed with 1-(dimethylamino)methyl-2-naphthol (98 mg) for 4 hours under an atmosphere of nitrogen. The mesitylene is then evaporated in vacuo and the residue is purified by preparative thin-layer chromatography on silica gel plates to isolate the title compound (95 mg), melting point 209°–212° C. with consistent spectral data.

EXAMPLE 4

17-(Ethylthio)-9-fluoro-2',3'-dihydro-11β-hydroxy-1'H-androsta-1,4-dieno[16α,17α-b]naphtho[1,2-e]pyran-3-one A solution of 17-(ethylthio)-9-fluoro-11β-hydroxyandrosta-1,4,16-triene-3-one (100 mg) in dry mesitylene (1.5 ml) is refluxed with 1-(dimethylamino)methyl-2-naphthol (100 mg) for 4 hours. The mesitylene is then evaporated in vacuo and the residue is subjected to preparative thin-layer chromatography on silica gel plates to afford the title compound (110 mg), melting point 155°–159° C. with consistent spectral data.

EXAMPLE 5

17-(Ethylsulfonyl)-9-fluoro-3',4'-dihydro-11β-hydroxy-2'H-androsta-1,4-dieno[17α,16α-b][1]benzopyran-3-one A solution of 17-(ethylthio)-9-fluoro-3',4'-dihydro-11β-hydroxy-2'H-androsta-1,4-dieno[17α,16α-b][1]benzopyran-3-one (400 mg, prepared as described in Example 2) in dry dichloromethane (70 ml) is stirred at room temperature for 4.0 hours after mixing with a solution of m-chloroperbenzoic acid (383 mg) in dichloromethane (30 ml). The resulting solution is washed with a saturated sodium bicarbonate solution and water, dried and evaporated to afford the title compound as a solid (420 mg), melting point 168°–170° C. with consistent spectral data.

EXAMPLES 6–11

Following the procedure of Example 2, but substituting the steroid of column I for 9-fluoro-11β-hydroxyandrosta-1,4-diene-3,17-dione, the compound of column II for ethanethiol and the compound of column III for o-dimethylaminomethylphenol, yields the steroid of column IV.

| | Column I | Column II | Column III | Column IV |
|---|---|---|---|---|
| 6 | 11β-hydroxyandrosta-1,4-diene-3,17-dione | n-butanethiol | 2-[1-(dimethylamino)ethyl]phenol | 17-(butylthio)-3',4'-dihydro-11β-hydroxy-4'-methyl-2'H-androsta-1,4-dieno[17α,16α-b][1]benzopyran-3-one |
| 7 | 9-iodo-11β-hydroxy-androsta-1,4-diene- | 1-mercapto-2-methylbenzene | 4,5-dimethyl-2-dimethylaminomethyl- | 9-iodo-3',4-40-dihydro-11β-hydroxy-6',7'-dimethyl-17-[(2-methyl- |

-continued

| Column I | Column II | Column III | Column IV |
|---|---|---|---|
| 3,17-dione | | phenol | phenyl)thiol-2'H-androsta-1,4-dieno[17α,16α-b][1]benzopyran-3-one |
| 8 9-chloro-11β-hydroxy-androstra-1,4-diene-3,17-dione | 1-chloro-4-mercaptobenzene | 4-chloro-2-dimethyl-aminomethylphenol | 6',9-dichloro-17-[(4-chlorophenyl)-thio]-3',4'-dihydro-11β-hydroxy-2'H-androsta-1,4-dieno[17α,16α-b]-[1]benzopyran-3-one |
| 9 6α,9-difluoro-11β-hydroxyandrosta-4-ene-3,17-dione | 1-mercapto-2-methoxybenzene | 3-methoxy-2-dimethyl-aminomethylphenol | 6α,9-difluoro-3',4'-dihydro-11β-hydroxy-5'-methoxy-17-[(2-methoxyphenyl)thio]-2'H-androsta-1,4-dieno[17α,16α-b][1]benzopyran-3-one |
| 10 9-bromo-11β-hydroxy-androsta-1,4-diene-3,17-dione | 1-mercapto-2,4-dimethylbenzene | 4-(t-butyl)-2-diethyl-aminomethylphenol | 9-bromo-6'-(t-butyl)-3',4'-dihydro-11β-hydroxy-17-[(2,4-dimethylphenyl)-thiol-2'H-androsta-1,4-dieno[17α-16α-b][1]benzopyran-3-one |
| 11 11β-hydroxy-6α-methyl-androsta-1,4-diene-3,17-dione | methanethiol | 2-bromo-4-methyl-6-dimethylaminomethyl-phenol | 8'-bromo-3',4'-dihydro-11β-hydroxy-6α,6'-dimethyl-17-(methylthio)-2'H-androsta-1,4-dieno[17α,16α-b]-[1]benzopyran-3-one |

What is claimed is:
1. A steroid having the formula

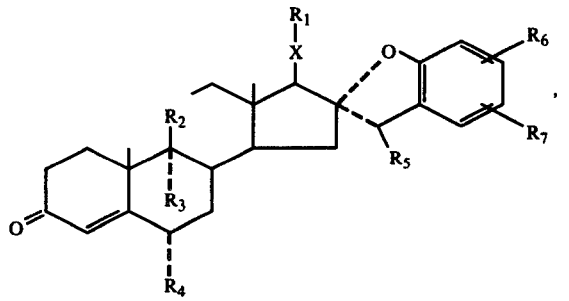

or a 1,2-dehydro derivative thereof, wherein X is —S—,

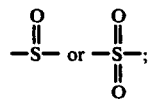

$R_1$ is alkyl, aryl or

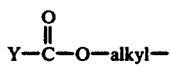

wherein Y is alkyl or aryl; $R_2$ is carbonyl or β-hydroxymethylene; $R_3$ is hydrogen or halogen; $R_4$ is hydrogen, fluorine or methyl; $R_5$ is hydrogen or alkyl; and $R_6$ and $R_7$ are the same or different and are hydrogen, halogen, alkyl or alkoxy, or $R_6$ and $R_7$ together with the benzene ring to which they are attached form a naphthalene group; wherein the term "aryl" refers to phenyl or phenyl substituted with 1 or 2 alkyl, alkoxy or halogen groups; and the terms "alkyl" and "alkoxy" refer to groups having 1 to 10 carbon atoms.

2. A steroid in accordance with claim 1 wherein $R_6$ and $R_7$ are the same or different and are hydrogen, halogen, alkyl or alkoxy.

3. A steroid in accordance with claim 1 wherein $R_6$ and $R_7$ together with the benzene ring to which they are attached form a naphthalene ring.

4. A steroid in accordance with claim 1 wherein X is —S—.

5. A steroid in accordance with claim 1 wherein X is

6. A steroid in accordance with claim 1 wherein X is

7. A steroid in accordance with claim 1 wherein $R_1$ is alkyl.

8. A steroid in accordance with claim 1 wherein $R_1$ is aryl.

9. A steroid in accordance with claim 1 wherein $R_1$ is

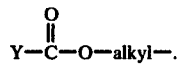

10. A steroid in accordance with claim 1 wherein $R_5$ is hydrogen.

11. A steroid in accordance with claim 1 wherein $R_2$ is β-hydroxymethylene, $R_3$ is fluorine, and $R_4$ is hydrogen.

12. A steroid in accordance with claim 1 wherein $R_5$ is hydrogen.

13. The steroid in accordance with claim 1, 17-[[(acetyloxy)methyl]thio]-9-fluoro-3',4'-dihydro-11β-hydroxy-2'H-androsta-1,4-dieno[17α,16α-b][1]benzopyran-3-one.

14. The steroid in accordance with claim 1, 17-(ethylthio)-9-fluoro-3',4'-dihydro-11β-hydroxy-2'H-androsta-1,4-dieno[17α,16α-b][1]benzopyran-3-one.

15. The steroid in accordance with claim 1, 17-(phenylthio)-9-fluoro-2',3'-dihydro-11β-hydroxy-1'H-androsta-1,4-dieno[16α,17α-b]naphtho[1,2-e]pyran-3-one.

16. The steroid in accordance with claim 1, 17-(ethylthio)-9-fluoro-2',3'-dihydro-11β-hydroxy-1'H-androsta-1,4-dieno[16α,17α-b]naphtho[1,2-e]pyran-3-one.

17. The steroid in accordance with claim 1, 17-(ethylsulfonyl)-9-fluoro-3',4'-dihydro-11-hydroxy-2'H-androsta-1,4-dieno[17α,16α-b][1]benzopyran-3-one.

* * * * *

UNITED STATES PATENT OFFICE
CERTIFICATE OF CORRECTION

Patent No. 4,146,538          Dated March 27, 1979

Inventor(s) Ravi K. Varma, Sam T. Chao

It is certified that error appears in the above-identified patent and that said Letters Patent are hereby corrected as shown below:

In the formula in the Abstract, in formula I (in column 1), in formula IX (in column 4) and in the formula in claim 1, that portion of the steroid structure shown as " 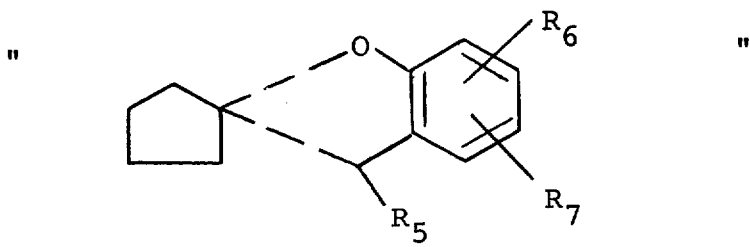 "

should read

UNITED STATES PATENT OFFICE
CERTIFICATE OF CORRECTION

Patent No. 4,146,538     Dated March 27, 1979

Inventor(s) Ravi K. Varma, Sam T. Chao

It is certified that error appears in the above-identified patent and that said Letters Patent are hereby corrected as shown below:

-- 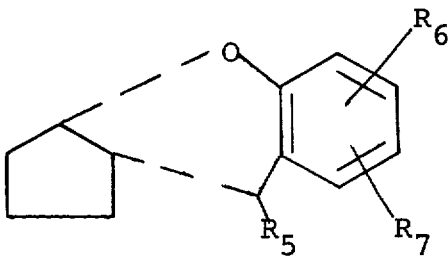 --

In the Table, Column IV, Example 7 "4-40" should read --,4'--

Signed and Sealed this

Thirty-first Day of July 1979

[SEAL]

Attest:

Attesting Officer

LUTRELLE F. PARKER
Acting Commissioner of Patents and Trademarks